(12) United States Patent
Preiss

(10) Patent No.: US 6,172,259 B1
(45) Date of Patent: Jan. 9, 2001

(54) PRODUCTION OF ENANTIOMER-FREE BIARYLKETOCARBOXYLIC ACIDS

(75) Inventor: Michael Preiss, Wuppertal (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/381,597

(22) PCT Filed: Apr. 14, 1998

(86) PCT No.: PCT/EP98/02176

§ 371 Date: Sep. 20, 1999

§ 102(e) Date: Sep. 20, 1999

(87) PCT Pub. No.: WO98/49124

PCT Pub. Date: Nov. 5, 1998

(30) Foreign Application Priority Data

Apr. 25, 1997 (DE) .............................. 197 17 429

(51) Int. Cl.$^7$ .......................... C07B 55/00; C07C 315/00
(52) U.S. Cl. ............................................ 562/401; 562/428
(58) Field of Search ..................................... 562/401, 428

(56) References Cited

FOREIGN PATENT DOCUMENTS

| 2809794 | 9/1978 | (DE) . |
|---|---|---|
| 3824353 | 1/1990 | (DE) . |
| 0298395 | 1/1989 | (EP) . |
| 0423467 | 4/1991 | (EP) . |
| 9615096 | 5/1996 | (WO) . |

OTHER PUBLICATIONS

Patent Abstracts of Japan, vol. 095, No. 009, Oct. 31, 1995, & JP 07 149688, (Teikoku Chem. Industry), Jun. 13, 1995.

*Primary Examiner*—Paul J. Killos
(74) *Attorney, Agent, or Firm*—Norris, McLaughlin & Marcus, P.A.

(57) ABSTRACT

The invention relates to a continuous process for the preparation of enantiomerically pure biarylketocarboxylic acids, S-phenylethylamine being employed as an auxiliary base in the resolution. Biarylketocarboxylic acids, in particular substituted biaryl-4-ketocarboxylic acids, are inhibitors of enzymes of the matrix metalloproteinases class. By inhibition of the abovementioned enzymes, it is possible, for example, to control osteoarthritis, rheumatoid arthritis and metastases.

1 Claim, No Drawings

PRODUCTION OF ENANTIOMER-FREE BIARYLKETOCARBOXYLIC ACIDS

The invention relates to a continuous process for the preparation of enantiomerically pure biarylketocarboxylic acids. Biarylketocarboxylic acids, in particular substituted biaryl-4-ketocarboxylic acids, are inhibitors of enzymes of the matrix metalloproteinases class. By inhibition of the abovementioned enzymes it is possible, for example, to control osteoarthritis, rheumatoid arthritis and metastases.

The biarylketocarboxylic acids are obtained on synthesis as racemates and these are described in WO 96/15096. The pharmacologically active enantiomer, which is contained in the racemates to 50%, is separated off from the racemates. It is thus very worthwhile to separate off the active enantiomer, of which anyway only theoretically 50% can be formed, in as high a yield as possible.

For enantiomer separations, optically active auxiliaries are employed which form a diastereomeric salt with the enantiomer to be separated off. Preferably, the diastereomeric salt should be more poorly soluble than the other reaction component so that it can be easily separated off. Preferably, the diastereomeric salt should be obtained in high enantiomeric purity even on preparation, so that subsequently as few additional purification steps as possible are necessary, whereby a high yield is achieved. Preferably, the optically active auxiliary should be present in chemically pure form having a defined content, and should be readily accessible and cost-effective. Preferably, only 50% of the optically active auxiliary should be employed, such that the diastereomeric salt is formed only with the desired enantiomer.

The prior art is the resolution of biarylketocarboxylic acids with cinchonine as described in WO 96/15096 as exemplified by 4-chlorobiphenyl-4-oxo-2-phenyl-thiomethylenebutane-carboxylic acid. 4 reaction steps are necessary in order to achieve an enantiomeric purity of over 99%; if the amounts used are increased 6 reaction steps are even necessary. The diastereomeric salt of the active enantiomer is admittedly less readily soluble than that of the inactive diastereomer, but the optical purification per reaction step is unsatisfactory. It is particularly unadvantageous that after each cleavage the acid has to be liberated from the salt and this has to be reacted again with cinchonine. The yield is only 28% of the batch. The purification steps are as follows:

1. Reaction of the racemate with cinchonine to give the salt
2. Liberation of the acid; enantiomer ratio 86:14
3. Reaction of the enriched acid with cinchonine to give the salt
4. Liberation of the acid; enantiomer ratio 96:4
5. Reaction of the enriched acid with cinchonine to give the salt
6. Liberation of the acid; enantiomer ratio 99.5:0.5.

The reason for the poor optical purification, inter alia, is to be sought in the optically active auxiliary base cinchonine employed here. Cinchonine is a non-homogeneous natural substance which contains 5 to 30% of dihydrocinchonine. Cinchonine can only be obtained in limited amounts and is moreover very expensive.

Experiments with other optically active auxiliary bases such as brucine, strychnine, quinine, cinchonidine and dehydroabietylamine afforded either only oils, homogeneous solutions or the salts with an enantiomer ratio differing only little from 1:1.

In the present invention, an efficient enantiomer separation of 4-chlorobiphenyl-4-oxo-2-phenylthiomethylene-butanecarboxylic acid using the readily accessible and inexpensive auxiliary base S-phenylethylamine is described.

It is to be denoted as extremely surprising that using the structurally very simple auxiliary base S-phenylethylamine an enantiomeric purity of 97 to 99% was achieved even in the preparation of the diasteriomeric salt. It was not foreseeable that the diastereomeric salt of the active enantiomer, on the one hand, would be so poorly soluble and, on the other hand, would crystallize out in such a high enantiomeric purity. It is furthermore advantageous that the diastereomeric salt, if desired, can be brought to an enantiomeric purity of 99 to 100% by a simple recrystallization (i.e. without prior liberation of the acid and subsequent fresh reaction with the auxiliary base). The yield amounts to 40%, i.e. theoretical 80%. It is furthermore advantageous that the diastereomeric salt of the inactive enantiomer can also be dissolved out using a smaller amount of solvent than necessary for the dissolution of the diasteriomeric salt mixture. The yield in this procedure increases to 42%, i.e. theoretical 84%.

The purification steps according to this process are as follows:

1. Reaction of the racemate with S-phenylethylamine to give the salt
2. Liberation of the acid; enantiomer ratio 97:3 to 99:1.

If appropriate, the recrystallization described above can be carried out between steps 1 and 2.

An additional advantage is that the racemate can be subjected to the enantiomer separation in situ, i.e. the last chemical step and the resolution are coupled with one another as is shown in the following reaction scheme. Biphenylacrylic acid (1) is reacted with thiophenol in the presence of tetrabutylammonium fluoride to give 4-chlorobiphenyl-4-oxo-2-phenylthiomethylene-butanecarboxylic acid (2) and this is reacted with S-phenylethylamine (S-PEA) without isolation to give the corresponding S-phenylethylammonium salt (1). 3 can optionally be recrystallized. The desired enantiomer of 4-chlorobiphenyl-4-oxo-2-phenylthiomethylene-butanecarboxylic acid (4) is then liberated from 3.

It is furthermore advantageous that the entire reaction sequence, i.e. the chemical step of thiophenol addition, the formation of the S-PEA salt, the recrystallization which is possibly to be carried out and the liberation of the desired enantiomer can be carried out in a single solvent (acetone).

It is furthermore advantageous that only 0.5 to 0.6 equivalents of the optically active base S-phenylethylamine have to be employed. Reaction scheme:

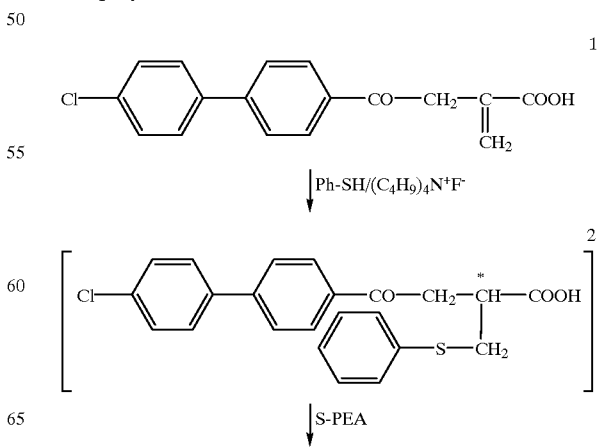

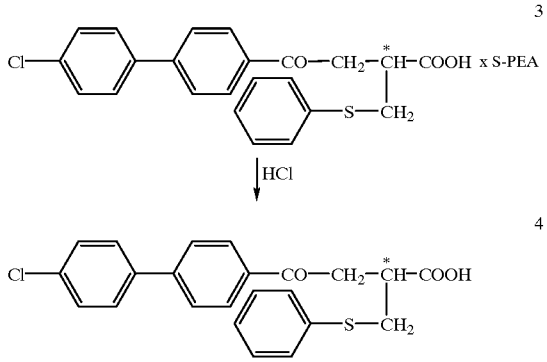

The concentration of the reaction solution can be 2 to 20%, preferably 12 to 16%.

The concentration of the recrystallization can be 2% up to saturation; however, substantially less solvent can also be used.

The ratio racemate to the auxiliary base S-PEA can be 0.45 to 1.00, preferably 0.5 to 0.6.

Solvents which can be employed are: ethers, such as, for example, diethyl ether, THF, dioxane, ethylene glycol dimethyl ether, ethylene glycol monomethyl ether, diethylene glycol dimethyl ether; ketones, such as, for example, acetone, methyl ethyl ketone, diethyl ketone, methyl isobutyl ketone; esters, such as, for example, methyl acetate, ethyl acetate and butyl acetate. THF, ethyl acetate and acetone are particularly preferred; acetone is very particularly preferred.

The abovementioned solvents can also be employed as mixtures. The same solvent can be employed for the thiophenol addition, for the enantiomer separation, for the recrystallization of the diastereomeric salts and for the liberation of the acid from the salt or different solvents can be employed. 1 to 30% of water can be added to the water-miscible solvents.

EXAMPLE 1

Preparation of 4-chlorobiphenyl-4-oxo-2-phenylthiomethylene-butanecarboxylic acid with recrystallization 246 g of 4-chlorobiphenyl-4-oxo-2-methylene-butanecarboxylic acid are initially introduced into 2.0 l of acetone. 10.1 g of tetrabutylammonium fluoride trihydrate and 92 ml of thiophenol are added thereto. The mixture is refluxed for 2.5 hours and cooled to 40 to 42° C. 54.5 g of (S)-(–)-1-phenylethylamine in 100 ml of acetone are then added in the course of 45 minutes. The mixture is then allowed to come to room temperature in the course of 2 hours and is stirred at room temperature for a further hour. The solid is filtered off with suction and washed with 500 ml of acetone. The moist precipitate is heated to reflux in 4.6 l of acetone (if appropriate more acetone is necessary depending on the residual moisture), and the solution is cooled to 46° C. and seeded. It is stirred for 2 hours (without heating), cooled to 5° C. and stirred for a further hour. The crystallizate is filtered off with suction and washed with 250 ml of acetone. The moist crystallizate is dissolved in a mixture of 200 ml of acetone and 55 ml of half-conc. hydrochloric acid, and the solution is brought to pH 1 to 2 using hydrochloric acid, filtered and added to 500 ml of 0.5 N hydrochloric acid cooled to 0 to –5° C., in which there are seed crystals, in the course of 30 minutes. The mixture is stirred at this temperature for a further 15 minutes, and the solid is filtered off with suction, washed with water and dried. 133 g (39.6% of theory) having an enantiomeric purity of over 99% are obtained.

EXAMPLE 2

Preparation of 4-chlorobiphenyl-4-oxo-2-phenylthiomethylene-butanecarboxylic acid without recrystallization 246 g of 4-chlorobiphenyl-4-oxo-2-methylene-butanecarboxylic acid are initially introduced into 2.0 l of acetone. 10.1 g of tetrabutylammonium fluoride trihydrate and 92 ml of thiophenol are added thereto. The mixture is refluxed for 2.5 hours and cooled to 40 to 42° C. 54.5 g of (S)-(–)-1-phenylethylamine in 100 ml of acetone are then added in the course of 45 minutes. The mixture is allowed to come to room temperature in the course of 2 hours and is stirred at room temperature for a further hour. The solid is filtered off with suction and washed with 500 ml of acetone. The moist crystallizate is dissolved in a mixture of 200 ml of acetone and 55 ml of half-conc. hydrochloric acid, and the solution is brought to pH 1 to 2 using hydrochloric acid, filtered and added to 500 ml of 0.5 N hydrochloric acid cooled to 0 to –5° C., in which there are seed crystals, in the course of 30 minutes. The mixture is stirred at this temperature for a further 15 minutes, and the solid is filtered off with suction, washed with water and dried. 135 g (40.2% of theory) having an enantiomeric purity of 97 to 99% are obtained.

EXAMPLE 3

Preparation of 4-chlorobiphenyl-4-oxo-2-phenylthiomethylene-butanecarboxylic acid with purification 246 g of 4-chlorobiphenyl-4-oxo-2-methylene-butanecarboxylic acid are initially introduced into 2.0 l of acetone. 10.1 g of tetrabutylammonium fluoride trihydrate and 92 ml of thiophenol are added thereto. The mixture is refluxed for 2.5 hours and cooled to 40 to 42° C. 54.5 g of (S)-(–)-1-phenylethylamine in 100 ml of acetone are then added in the course of 45 minutes. The mixture is allowed to come to room temperature in the course of 2 hours and is stirred at room temperature for a further hour. The solid is filtered off with suction and washed with 500 ml of acetone. The moist precipitate is kept at reflux for 30 min in 2.0 l of acetone. The mixture is cooled to 5° C. and kept at this temperature for 1 hour. The crystallizate is filtered off with suction and washed with 250 ml of acetone. The moist crystallizate is dissolved in a mixture of 200 ml of acetone and 55 ml of half-conc. hydrochloric acid, and the solution is brought to pH 1 to 2 using hydrochloric acid, filtered and added to 500 ml of 0.5 N hydrochloric acid cooled to 0 to –5° C., in which there are seed crystals, in the course of 30 min. The mixture is stirred at this temperature for a further 15 min, and the solid is filtered off with suction, washed with water and dried. 141 g (42.0% of theory) having an enantiomeric purity of over 99% are obtained.

What is claimed is:

1. Process for the preparation of enantiomerically pure biarylketocarboxylic acids, characterized in that the auxiliary base used in the resolution is S-phenylethyl-amine.

* * * * *